United States Patent [19]

Finke et al.

[11] Patent Number: 4,797,396

[45] Date of Patent: Jan. 10, 1989

[54] β-LACTAM DERIVATIVES AS ANTI-INFLAMMATORY AND ANTIDEGENERATIVE AGENTS

[75] Inventors: Paul E. Finke, Milltown; Morris Zimmerman, Watchung; James B. Doherty, New Milford; Bonnie Mae Ashe, Scotch Plains; Conrad P. Dorn, Plainfield, all of N.J.

[73] Assignee: Merck & Co., Inc., Rahway, N.J.

[21] Appl. No.: 74,440

[22] Filed: Jul. 16, 1987

Related U.S. Application Data

[62] Division of Ser. No. 627,166, Jul. 2, 1984, Pat. No. 4,711,886.

[51] Int. Cl.$^4$ .................. C07D 487/04; A61K 31/42
[52] U.S. Cl. .................. 514/210; 540/310; 540/349; 540/348; 514/192; 514/195
[58] Field of Search .................. 540/310, 349, 348; 514/195, 192, 210

[56] References Cited

U.S. PATENT DOCUMENTS

| 4,431,658 | 2/1984 | Afonso et al. | 540/310 |
| 4,650,795 | 3/1987 | Liberman et al. | 514/210 |
| 4,717,722 | 1/1988 | Doherty et al. | 514/210 |

Primary Examiner—Nicholas S. Rizzo
Attorney, Agent, or Firm—Theresa Y. Cheng; Michael C. Sudol

[57] ABSTRACT

β-Lactam derivatives and analogs are found to be potent elastase inhibitors and thereby useful anti-inflammatory/antidegenerative agents.

3 Claims, No Drawings

β-LACTAM DERIVATIVES AS ANTI-INFLAMMATORY AND ANTIDEGENERATIVE AGENTS

This is continuation division of application Ser. No. 627,166 filed 7/2/84, now U.S. Pat. No. 4,711,886.

BACKGROUND OF THE INVENTION

We have found that β-lactam derivatives and analogs are potent elastase inhibitors and therefore are useful anti-inflammatory/anti-degenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occur during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and B. Ashe et al., *J. Biol. Chem.*, 256, 11603 (1981);

(3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelberg, N.Y., 1979, pp. 196–206.

Accordingly, an object of this invention is to discover new protease inhibitors, especially elastase inhibitors, useful for controlling tissue damage and various inflammatory or degenerative conditions mediated by proteases particularly elastase.

Another object of the present invention is to provide pharmaceutical compositions for administering the active β-lactam derivatives and analogs as protease inhibitors.

Still a further object of this invention is to provide a method of controlling inflammatory conditions by administering a sufficient amount of one or more of the active, β-lactam derivatives and analogs in a mammalian species in need of such treatment.

DETAILED DESCRIPTION OF THE INVENTION

A Scope of the Present Invention

This invention relates to β-lactam derivatives especially penem and analogs which are potent elastase inhibitors useful in the prevention, control and treatment of inflammatory conditions especially arthritis and emphysema.

Free acids of penem derivatives and analogs are known antibiotics which have been described in various patents. For example, U.S. Pat. Nos. 4,260,618; 4,301,074; G.B. Pat. Nos. 201 3674 and 204 3639.

The compounds of the present invention are of formula:

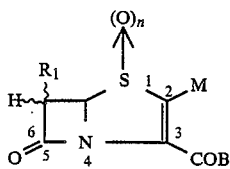
(I)

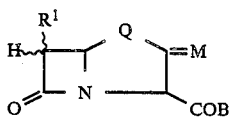
(II)

wherein
Q is O or S;
n is 0, 1 or 2.
Preferably Q is O, n is 0 or 1.
For structure (I),
M is:
(1) —OR wherein R is as defined below;
(2) —SR;
(3) —S(O)R;
(4) —SO$_2$R or —SO$_3$R;;
(5) —COOR;
(6) —OCOR or —OCOOR;
(7) phenyl;
(8) —CH$_2$A wherein A represents
  (a) hydrogen;
  (b) loweralkyl especially C$_{1-6}$alkyl;
  (c) hydroxy;
  (d) alkoxy;
  (e) aryloxy;
  (f) aralkyloxy;
  (g) —SR;
  (h) acylthio;
  (i) acyloxy especially alkanoyloxy or arylcarbonyloxy such as acetoxy, benzyloxycarbonyloxy, benzoyloxy; and succinoyloxy; substituted or unsubstituted carbamoyl, thiocarbamoyl and N-alkyl or N,N-dialkyl derivatives thereof;
  (j) a quaternary ammonium group, for example, —N$^+$H$_3$, —N$^+$HE$^2$, or —N$^+$E$^3$ where E represents loweralkyl, aryl or aralkyl;
  (k) unsubstituted or substituted amino or amido group especially —NH$_2$, —CONH$_2$ and N-alkyl or N,N-dialkyl derivatives thereof.
  (l) —CH$_2$N$_3$;
  (m) halo;
  (n) —CH$_2$NH$_2$;
  (o) —CH$_2$NHCOOR
  (p) —CH$_2$NHCOR wherein R is:
    (i) straight or branched alkyl chain having from 1 to 10 carbon atoms especially methyl, ethyl, isopropyl, t-butyl, pentyl, or hexyl;
    (ii) aryl having from 6 to 10 carbon atoms especially phenyl, substituted phenyl or naphthalene;
    (iii) cycloalkyl having from 3 to 8 carbon atoms especially cyclopentyl, or cyclohexyl;
    (iv) alkenyl having from 2 to 20 carbon atoms especially C$_{2-6}$alkenyl such as vinyl, allyl, or butenyl;
    (v) cycloalkenyl having from 5 to 8 carbon atoms especialy cyclopentenyl or cyclohexenyl;
    (vi) alkynyl having from 2 to 20 carbon atoms especially C$_{2-6}$alkynyl for example, ethynyl, propynyl or hexynyl;
    (vii) aralkyl, alkaryl, aralkenyl, aralkynyl, alkenylaryl or alkynylaryl wherein alkyl, aryl, alkenyl and alkynyl are as previously defined;
    (viii) monoheteroaryl, di- or polyheteroaryl, or fused heteroaryl containing from 1 to 3 of any one or more of the heteroatoms N, S or O in each heteroaryl ring thereof, for example, pyridyl, pyrryl, thienyl, isothiazolyl, imidazolyl, pyrazinyl, pyrimidyl quinolyl, isoquinolyl, benzothienyl, tetrazolyl, isobenzofuryl pyrazolyl, indolyl, purinyl, carbozolyl, isoxazolyl and the like;
    (ix) heteroarylalkyl such as
      2-pyridylmethyl,
      1-methyl-5-tetrazolyl,
      2-thienylmethyl and
      3-isothiazolylethyl; or
    (x) hydrogen;

the above groups (i)-(x) can be unsubstituted or can be substituted by radicals such as alkyl, alkoxy, halo such as fluoro, chloro, bromo or iodo, cyano, carboxy, sulfoamino, carbamoyl, alkyl or aminosulfonyl, azido, substituted amidino, amino, substituted amino such as monoalkylamino and dialkylamino, haloalkyl, carboxyalkyl, carbamoylalkyl, N-substituted carbamoylalkyl, —NHCOOCH$_3$, guanidino, N-substituted guanidino, guanidinoalkyl, carboxamidino, N-substituted carboxamidino, tetrazolyl, and the like.
(9) hydrogen;
(10) trifluoromethyl;
(11) halo such as Cl or F;
(12) —CHO;
(13)

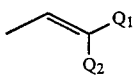

wherein Q$_1$ and Q$_2$ independently are CN, or COOR$_a$.
Preferably, R is:
(a) H;
(b) C$_{1-6}$alkyl;
(c) phenyl;
(d) —CH$_2$CH$_2$NH$_2$;
(e) —CH$_2$CH$_2$NH-COOCH$_3$;
(f) —CH$_2$CH$_2$OCH$_3$;
(g)

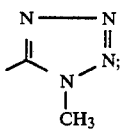

Thus, CH$_2$A can be a halomethyl such as chloromethyl, bromomethyl or fluoromethyl. When CH$_2$A is a substituted hydroxy or substituted mercapto group, it can be shown by the formula

—CH$_2$ZR$_5$ where Z is oxygen or sulfur, and R$_5$ is an acyl group; a straight chain or branched chain loweralkyl, alkenyl or alkynyl group; an aryl group; an aralkyl group; or a heterocyclic group such as heteroaryl, heterocycloalkyl e.g., 1,3-dioxacyclohex-4-yl, piperidino, morpholino, oxacyclopropyl, pyrrolidino, tetrazolo, benzothiazolo, imidazolidino, pyrazolidino, and piperazino; or heterocycloalkenyl such as pyrrolino, 2-imidazolino, 3-pyrazolino or isoindolino. These groups can be unsubstituted or can be substituted by radicals such as alkyl, alkoxy, halo, cyano, carboxy, carbamoyl, azido,, sulfo, amino,, substituted amino, haloalkyl, carboxyalkyl, carbamoylalkyl, N-substituted carbamoylalkyl, guanidino, N-substituted guanidino, guanidoalkyl, sulfamyl, substituted sulfamyl, and the like. Representative of the —CH$_2$A groups are methoxymethyl, n-propoxymethyl, methylthiomethyl, acetoxymethyl, propionyloxymethyl, benzoyloxymethyl, (p-chlorobenzoyl)oxymethyl, succinoyloxymethyl, (p-methylbenzoyl)oxymethyl, pivaloyloxymethyl, D- or L-α-aminophenylacetyloxy, (1-adamantyl)-carboxymethyl, butanoyloxymethyl, carbamoyloxymethyl, (N-methylcarbamoyl)oxymethyl, (N-ethylcarbamoyl)oxymethyl, [N-(2-chloroethyl)carbamoyl]oxymethyl, (N-phenylcarbamoyl)oxymethyl, [N-(carboxymethyl)carbamoyl]oxymethyl, (N-p-sulfophenyl-carbamoyl)oxymethyl, (N-p-carboxymethylphenyl-carbamoyl)oxymethyl, methoxycarbonyloxymethyl, isobutanoyloxymethyl, cyclobutyl-carbonyloxymethyl, carbamoylthiomethyl, (ethoxythiocarbonyl)thiomethyl, (n-propoxythiocarbonyl)thiomethyl, (cyclopentanoxythiocarbonyl)thiomethyl, methylthiomethyl, N,N-diethylthiocarbamoylthiomethyl, N-methyl(e) piperazinium-1-thiocarbonylthiomethyl, N,N-dimethylpiperazinium-1-thiocarbonylthiomethyl, 2-furoylthiomethyl, isothiouroniummethyl, (5-methyl-1,3,4-thiadiazol-2-yl)thiomethyl, p-tolylsulfonylthiomethyl, 2-benzohiazolothiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl.

Alternatively, when CH$_2$A is hydroxymethyl, the penem derivative or analog can also exist as the lactone which is formed by internal esterification with the adjacent carboxy group.

The substituent CH$_2$A can also be a group of the general formula

—CH$_2$Y$_1$ wherein Y$_1$ represents amino or substitued amino including nitrogen heterocycles and substituted heterocyclic groups as described for R$_5$. Y$_1$ may also be nitrogen which is part of the heterocyclic system as shown below. Examples of such groups that might be mentioned are aminomethyl, acetamidomethyl, carbamoylaminomethyl, N,N-dimethylaminomethyl, N-(2-chloroethyl)aminomethyl, 5-cyano-triazol-1-yl-methyl, 4-methoxycarbonyltriazol-1-yl-methyl.

When A is amino the penem derivative or analog can also exist as the lactam formed by loss of water with the adjacent carboxy group.

Representative of the quaternary ammonium groups representing A that might be mentioned are pyridinium, 3-methylpyridinium, 4-methylpyridinium, 3-chloropyridinium, 3-bromopyridinium, 3-iodopyrinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-carboxymethylpyridinium, 4-hydroxymethylpyridinium, 4-trifluoromethyl-pyridinium, quinolinium, picolinium and lutidinium.

When A is mercapto,i.e., —SR, it may be —SH,

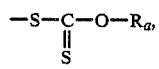

heteroaryl containing nitrogen such as:

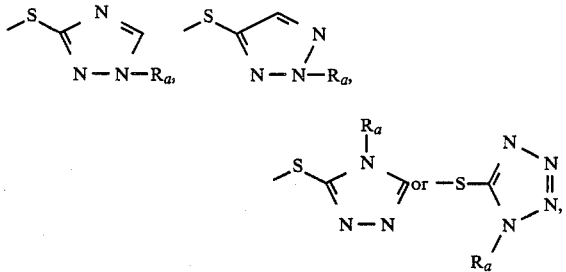

alkylthio, arylthio, aralkylthio or heterocyclothio, wherein R$_a$ represents C$_{1-6}$alkyl or H.

The preferred groups representing A are
(a) hydrogen;
(b) C$_{1-6}$ alkyl
(c) phenyl;
(d) OR;
(e) halo;
(f) OCOR;
(g) SR,

or —SCOOR$_a$, especially —SCH$_3$, —SC$_2$H$_5$—, —S-COOC$_2$H$_5$,

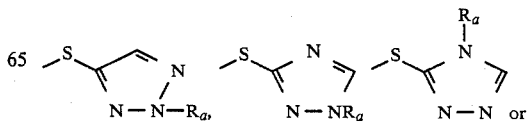

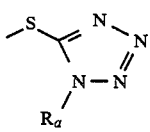

(h) acylthio, i.e., —SCOR;
(i) CH₂NHCHO;
(j) —CH₂N₃;
(k) CH₂NH₂; or
(l) CH₂OH.

The acyl group RCO— can be a loweralkanoyl group of 2-6 carbon atoms such as acetyl, —COC₂H₅ or —COC₃H₇, carbamoyl, or thiocarbamoyl and N-alkyl or N,N-dialkyl derivatives thereof. The alkyl group of the foregoing substituents contains 1-10 carbon atoms and may be further substituted by radicals such as alkoxy, halo, amino, cyano, carboxy, sulfo, and the like.

More preferably, A is
(a) OCOR, i.e., alkanoxyloxy especially

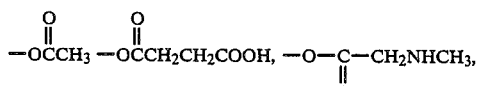

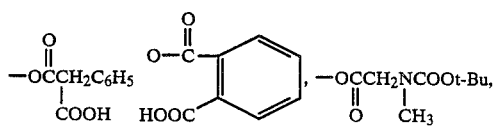

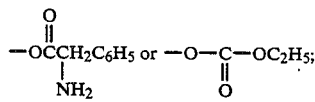

(b) C₁₋₃alkoxy especially methoxy, ethoxy or i- or n-propyloxy;
(c) phenyl;
(d) hydrogen;
(e) hydroxy; or
(f) SR or

For structure (II),
M can only be =O, =S, or =CHA;
R₁ is
  (a) nitrogen bonded group including R'NH— wherein R' is as defined below;
  (b) hydrogen;
  (c) hydroxy;
  (d) mercapto;
  (e) substituted oxy;
  (f) substituted thio;
  (g) hydrocarbyl or substituted hydrocarbyl group;
  (h) cyano;
  (i) carbonyl or thiocarbonyl containing substituents bonded by said carbonyl or thiocarbonyl radical;
  (j) halo;
  (k) phosphono or a substituted phosphono group; or
  (l) hydroxyalkyl especially hydroxy-C₁₋₆alkyl such as CH₃CH(OH)—;
  (m) alkoxycarbonyloxyalkyl especially C₁₋₆alkoxycarbonyloxy C₁₋₆alkyl such as CH₃CH(OCOOt—Bu)—;
  (n) benzoxycarbonyloxy-C₁₋₆alkyl, e.g., CH₃CH(OCOOCH₂C₆H₅)—;
  (o) phenoxycarbonyloxy-C₁₋₆alkyl such as CH₃CH(OCOOC₆H₅)—; or
  (p) alkoxycarbonylalkyl.

When R₁ is R'NH—, R' represents a substituted or unsubsrituted aliphatic, aromatic or heerocyclic, araliphatic or heterocyclylaliphatic carboxylic acid radical or a carbothioic acid radical such as the acyl radicals of the known cephalosporins and penicillins. These acyl radicals can be represented by the general formula

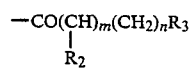

where R₂ is a radical of the group defined below, m and n represent 0–4 and R₃ represents R″ or ZR″, which are also defined below.

One group of the acyl radicals, i.e., when m and n are both 0 and R₃ is R″, can be represented by the general formula

wherein R″ is:
  (a) straight or branched chain alkyl having from 1 to 20 carbon atoms especially methyl, trifluoromethyl, ethyl, isopropyl, t-butyl, pentyl or hexyl;
  (b) aryl having trom 6 to 10 carbon atoms especially phenyl, substituted phenyl or naphthalene;
  (c) cycloalkyl having from 3 to 8 carbon atoms especially cyclopentyl, or cyclohexyl;
  (d) alkenyl having from 2 to 20 carbon atoms especially C₂₋₆alkenyl such as vinyl, allyl, or butenyl;
  (e) cycloalkenyl having from 5 to 8 carbon atoms especially cyclopentenyl or cyclohexenyl;
  (f) alkynyl having from 2 to 20 carbon atoms especially C₂₋₆alkynyl for example, ethynyl, propynyl or hexynyl;
  (g) alkoxy having from 1 to 10 carbon atoms especially C₁₋₃ alkoxy such as methoxy, ethoxy or n-propoxy or i-propoxy;
  (h) aralkyl, alkyryl, aralkenyl, aralkynyl, alkenylaryl or alkynylaryl wherein alkyl, aryl, alkenyl and alkynyl are as previously defined;
  (i) monoheteroaral, di- or polyheteroaryl, or fused heteroaryl containing from 1 to 3 of any one or more of the heteroatoms N, S or O in each heteroaryl ring thereof, for example, pyridyl, pyrryl, thienyl, isothiazolyl, imidazolyl, pyrazinyl, pyrimidyl quinolyl, isoquinolyl, benzothienyl, isobenzofuryl pyrazolyl, indolyl, purinyl, carbozolyl, isoxazolyl and the like;
  (j) heteroarylalkyl such as 2-pyridylmethyl, 2-thienylmethyl and 3-isothiazolylethyl; or
  (k) hydrogen.

The above groups (a)–(b) can be unsubstituted or can be substituted by radicals such as alkyl, alkoxy, halo such as fluoro, chloro, bromo or iodo, cyano, carboxy, sulfoamino, carbamoyl, sulfonyl, azido, amino, substituted amino such as monoalkylamino and dialkylamino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R" is methoxy, ethoxy, benzyl, p-hydroxybenzyl, 3- or 4-nitrobenzyl, p-aminobenzyl, o-aminobenzyl, m-aminobenzyl, o-sulfobenzyl, p-carboxymethylbenzyl, p-carbamoylmethylbenzyl, m-fluorobenzyl, m-bromobenzyl, p-chlorobenzyl, p-methoxybenzyl, p-aminomethylbenzyl, hydrogen, methyl, ethyl, cyanomethyl, 2-pentenyl, n-amyl, n-heptyl, phenethyl, difluoromethyl, trifluoromethyl, dichloromethyl, dibromoethyl, 1-(3-methylimidazolyl)-methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, and tetrazolylmethyl. The term "sulfo" represents mercapto or thio, sulfinyl and sulfonyl.

The acyl group can also be a radical of the formula

wherein n is 0–4, Z represents oxygen, sulfur or nitrogen, and R" is defined as above. Representative members of the substituent

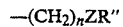

are allylthiomethyl, allylaminomethyl, phenylthiomethyl, butylmercaptomethyl, α-chlorocrotylmercaptomethyl, phenoxymethyl, phenylaminomethyl, phenoxyethyl, phenoxybutyl, phenoxybenzyl,, diphenoxymethyl, dimethylmethoxymethyl, dimethylbutoxymethyl, dimethylphenoxymethyl. 4-guanidinophenoxymethyl, 4-pyridylthiomethyl, p-(carboxymethyl)-phenoxymethyl, p-(carboxymethyl)phenylthiomethyl, 2-thiazolylthiomethyl, p-(sulfo)phenoxymethyl, p-(sulfo)phenylthiomethyl, p-(carboxy)phenoxymethyl, p-(carboxy)phenylthiomethyl, p-(carboxymethyl)phenoxymethyl, p-carboxymethyl)phenylthiomethyl, 2-pyrimidinylthiomethyl, phenethylthiomethyl, 1-(5,,6,7,8-tetrahydronaphthyl)oxomethyl, 6,8-bis(methylthio)octanoyl.

Furthermore, the acyl group can be a radical of the formula

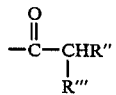

wherein R" is defined as above and R'" is a radical such as amino, hydroxy, azido, carbamoyl, guanidino, alkanoyloxy, halo, sulfamino, tetrazolyl, sulfo, carboxy, carbalkoxy, and the like. Representative members of the substituent

are α-aminobenzyl, α-amino-2-thienyl, α-methylaminobenzyl, α-amino-γ-methylmercaptopropyl, α-amino-3 or 4-chlorobenzyl, α-amino-3 or 4-hydroxybenzyl, α-amino-2,4-dichlorobenzyl, α-amino-3,4-dichlorobenzyl, D(—),-α-hydroxybenzyl, α-carboxybenzyl, α-amino-3-thienyl, α-amino-2-thienyl, D(—)-α-amino-3-chloro-4-hydroxybenzyl, D(—)-α-amino-3-thienyl, 1-aminocyclohexyl, α-(5-tetrazolyl)benzyl, α-sulfaminobenzyl, α-sulfamino-3-thienyl, α-(N-methylsulfamino)benzyl, D(—)-α-guanidino-2-thienyl, D(—)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-oxadiazolyl)-carboxymethyl, 4-(5-methoxy-1,3-sulfadiazolyl)-aminomethyl, 4-(5-methoxy-1,3-sulfadiazolyl)-hydroxymethyl, 4-(5-methoxy-1,3-sulfadiazolyl)-carboxymethyl, 2-(5-chlorothienyl)-aminomethyl, 2-(5-chlorothienyl)hydroxymethyl, 2-(5-chlorothienyl)-carboxymethyl, 3-(1,2-thiazolyl)aminomethyl, 3-(1,2-thiazolyl)hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymetnyl, 2-benzothienylaminomethyl, 2-benzothienylhydroxymethyl, 2-benzothienylcarboxymethyl, 2-azidooctyl-3-phenyl-3-azidomethyl, α-sulfobenzyl, and α-phosphonobenzyl.

Alternatively, the group

can be an unsubstituted or substituted alkyl or aryl sulfonamido group wherein R' is $C_{1-6}$alkyl-$SO_2$; $CF_3SO_2$; $C_6H_5SO_2$; or $C_6H_5CH_2SO_2$. For example, phenylsulfonamido, ethylsulfonamido, trifluoromethane sulfonamido, benzylsulfonamido, 2,5-dimethylsulfonamido, 4-chlorophenylsulfonamido, 4-methoxyphenylsulfonamido, or an unsubstituted or substituted alkyl or aryl sulfonylalkylamino group wherein R' is $CH_3SO_2CH(CH_3)$— or $C_6H_5SO_2CH_2$, and the like.

Preferably, R' is
(1) hydrogen;
(2)

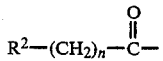

where
$R^2$ represents:
(a) hydrogen;
(b) methyl or substituted methyl such as trifluoromethyl, cyanomethyl a methoxymethyl;
(c) thienyl;
(d) phenyl; or
(e) mono- and disubstituted phenyl and thienyl wherein the substituents are selected from the group consisting of chloro, bromo, fluoro, nitro, loweralkyl, and loweralkoxy;
n is 0 or 1; or
(3)

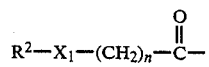

where
$X_1$ is oxygen or sulfur;
$R^2$ and n are as previously defined.
Even more preferably, R' is

$R^2$ being selected from the group consisting of:
(1) trifluoromethyl;
(2) methyl;
(3) methoxy;
(4) hydrogen;
(5) benzyl;
(6) phenyl;
(7) 2-thienylmethyl;
(8) phenylthiomethyl;
(9) phenoxymethyl;
(10) benzyloxy, or
(11) $NCCH_2SCH_2$ The oxy or thio substituent represented by $R_1$ can be a substituted hydroxy or mercapto group such as $-XR'_1$ wherein X is oxygen or sulfur and $R'_1$ is a hydrocarbyl group, preferably a straight or branched loweralkyl group of 1-6 carbon atoms, a straight or branched chain loweralkenyl or lower-alkynyl group of 3-6 carbon atoms, a monocyclic aryl group such as phenyl, furyl, pyrryl and pyridyl, or an aralkyl group such as benzyl. These alkyl, alkenyl, alkynyl, aryl or aralkyl groups can be substituted with groups such as hydroxy, halo, nitro, amino, carboxy, thio, and the like. Other specific substituents represented by $R_1$ that might be mentioned are groups of the formula $-OAc$, $-SAc$, $-SO_3H$, $-SO_2NH_2$, $-OCD_3$, $-SO_2R_2$, $-SO_2NR_3R_4$, $-OCOOR_2$, $-SOR_2^-$, $-OCOSR_2$, $-O-CONR_3R_4$, and the like wherein Ac represents an acyl group such as a formyl or lower-alkanoyl, $R_3$ and $R_4$ represent hydrogen, lower-alkyl, acyl and loweralkoxy, and $R_2$ represents loweralkyl, haloloweralkyl, aryl, aralkyl and substituted derivatives of such groups.

When $R_1$ is hydrocarbyl it can be straight or branched loweralkyl, straight or branched lower-alkenyl, loweralkynyl, aralkyl, cycloalkyl, a monocyclic aryl group, or a monocyclic heterocyclic group which can also be substituted with one or more groups such as halo, hydroxy, alkoxy, amino, nitro, sulfonyl, sulfamoyl, acyloxy, carbamoyloxy, carboxy, carboxamido and N-substituted carboxamido. Representative examples of such groups are $C_{1-6}$ alkyl such as methyl, trifluoromethyl, ethyl, n-propyl, isopropyl, t-butyl; $C_{2-6}$ alkenyl especially allyl, α-butenyl; $C_{2-6}$ alkynyl such as ethynyl and methylethynyl; loweraralkyl such as benzyl, p-methoxybenzyl, phenethyl; phenyl, p-aminophenyl; cyclopropyl, cyclopentyl and 4-hydroxycyclohexyl;

$R_1$ may also represent cyano or a group of the general formula

wherein X' is oxygen or sulfur, and R" is hydrogen, halo, hydroxy, mercapto, amino, substituted amino, alkyl, aryl, aralkyl, aralkoxy such as benzyloxy, alkoxy or aryloxy such as phenoxy, pyrroloxy, furyloxy, and thienyloxy, alkylthio or arylthio. Examples of these substituents are $-COOH$, $-CSSH$, $-COR_2$, $-COOR_2$, $-COSR_2$, $-CSSR_2$, $-CONH_2$, $-CSNH_2$, $-CSR_2$, $-CONHR_2$, $-CSNH$, $-CONR_3R_4$ and $-CSNR_3R_4$ wherein $R_2$ represents a straight or branched chain alkyl group of 1-6 carbon atoms and $R_3$ and $R_4$ represent hydrogen or $R_2$;

Furthermore, $R_1$ represents a nitrogen bonded group such as amino, substituted amino groups, nitro, azido, nitroso, isocyanato, isothiocyanato and hydroxyamino. Specific examples of nitrogen bonded groups that might be mentioned are $-N_3$, $-NH_2$, $-NHR_2$, $NR_2R_3$, wherein $R_2$ represents a straight or branched chain loweralkyl group of 1 to 6 carbon atoms, $R_3$ represents $R_2$ or hydrogen, and n represents the integer 1 or 2.

Finally, the substituent $R_1$ represents phosphono or a metal or ammonium salt thereof, or a substituted phosphono group of the formula:

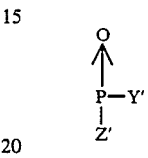

where Y' and Z' are the same or different and represent $-OR_2$, $-NR_3R_4$,

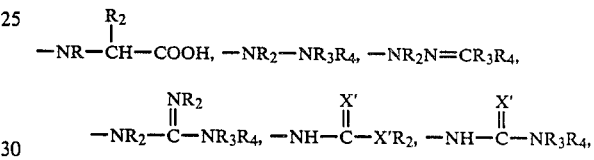

$-NC=X'$, $-OCOR_2$ and $-N_3$, where
$R_2$ represents hydrogen or a hydrocarbyl radical, $R_3$ and $R_4$ represent hydrogen, hydrocarbyl, alkoxy or an acyl radical, and X' represents oxygen or sulfur.

Preferably, $R_1$ is
(1) R'NH wherein R' is
  (a) hydrogen;
  (b) $CF_3CO$ or $CH_3OCO$;
  (c) $C_{1-6}$ alkyl $SO_2$;
  (d) $C_6H_5CH_2SO_2$;
(2) $C_{1-6}$alkoxycarbonyloxy$C_{1-6}$alkyl;
(3) benzoxycarbonyloxy$C_{1-6}$alkyl;
(4) hydroxyalkyl;
(5) OR where R is as previously defined;
(6) SR;
(7) hydrogen;
(8) $C_{1-6}$alkyl;
(9) $C_{1-6}$ alkoxycarbonyl $C_{1-6}$ alkyl; or
(10) phenoxycarbonyloxy $C_{1-6}$ alkyl.

Even more preferably, $R_1$ is
(1) $C_{1-3}$alkyl especially ethyl and isopropyl;
(2) hydroxy $C_{1-3}$alkyl especially $CH_3CH(OH)-$;
(3) OR where R is
  (a) $C_{1-6}$ alkyl especially methyl, ethyl, i-propyl; or
  (b)

where R represents hydrogen, $C_{1-6}$alkyl, phenyl, substituted or unsubstituted benzyl, or $C_{1-6}$alkylamino such as $CH_3NH-$, $C_2H_5NH-$;
(4) benzoxycarbonyloxy $C_{1-3}$alkyl, e.g., $CH_3CH(OCOOCH_2C_6H_5)-$;
(5) hydrogen; or
(6) $C_{1-6}$ alkoxycarbonyl $C_{1-3}$ alkyl.

B represents $OB_1$, or $NB_2B_3$ wherein $B_1$ and $B_2$ independently are:
  (a) straight or branched chain alkyl having from 1 to 20 carbon atoms, ethyl, isopropyl, t-butyl, pentyl or hexyl;
  (b) aryl having from 6 to 10 carbon atoms;
  (c) cycloalkyl having from 3 to 8 carbon atoms;
  (d) alkenyl having from 2 to 20 carbon atoms;
  (e) cycloalkenyl having from 5 to 8 carbon atoms;
  (f) alkynyl having from 2 to 20 carbon atoms;
  (g) aralkyl, alkaryl, aralkenyl, aralkynyl, alkenylaryl or alkynylaryl wherein alkyl, aryl, alkenyl and alkynyl are as previously defined;
  (h) loweralkenylalkyl;
  (i) alkanoylalkyl;
  (j) alkanoyloxyalkyl;
  (k) alkoxyalkyl;
  (1) a heterocyclic group including heterocyclic alkyl or heterocyclic alkenyl.

The above groups (a)-(1) can be unsubstituted or can be substituted by radicals such as alkyl, hydroxy, alkoxy, halo, nitro, mercapto, amino, substituted amino, cyano, carboxy, sulfoamino, carbamoyl, carbamoyloxy, alkyl or amino sulfonyl, alkyl or amino sulfinyl, sulfamoyl, azido, amino, substituted amino, carboxamido or N-substituted carboxamido; and $B_3$ is hydrogen or $B_1$. Representative examples of such groups are $C_{1-6}$ alkyl especially methyl, ethyl or t-butyl, allyl, 3-butenyl, methoxyethyl, benzyl, p-carbomethoxybenzyl, m-carbomethoxybenzyl, p-sulfonylbenzyl, m-fluorobenzyl, o,p-dinitrobenzyl, o,p-dichlorobenzyl, p-methylbenzyl, m-methoxybenzyl, o-methylthiobenzyl, benzhydryl, $CH_2CH_2CH_2COOCH_3$, $-CH_2COOC_2H_5$, and the like.

Preferably $B_1$ and $B_2$ independently are substituted or unsubstituted
  (1) aralkyl;
  (2) aryl;
  (3) straight or branched loweralkyl;
  (4) straight or branched loweralkenyl;
  (5) cycloalkyl;
  (6) alkanoyloxyloweralkyl;
  (7) alkanoylloweralkyl;
  (8) alkoxyloweralkyl; or
  (9) haloalkyl; and
$B_3$ is H or $B_1$.

Even more preferably, $B_1$ and $B_2$ independently are substituted or unsubstituted
  (1) benzyl such as p-nitrobenzyl;
  (2) ethyl;
  (3) t-butyl;
  (4) $-CH_2CH_2CH=CH_2$ or $CH_2-CH=C(CH_3)_2$;
  (5) $-CH_2CH_2CH_2COOt-Bu$;
  (6) alkanoyloxymethyl; or
  (7) alkanoylmethyl; and
$B_3$ is H or $B_1$.

It should be noted that the $\beta$-lactam derivatives can be active elastase inhibitors in the form of an optical isomer, for example, 1-, d- or dl-forms.

B. Preparation of The Compounds Within The Scope of the Invention

The penem derivatives and analogs of formula (I) or (II) where $OB_l$ is other than hydroxy can be prepared from the corresponding acid according to conventional methods of esterification. For example, (1) A compound of formula (I) or (II) wherein B is OH is treated with a lower alkanol, a substituted or unsubstituted benzyl alcohol, or a substituted or unsubstituted benzhydrol (diphenylmethanol) in the presence of a catalyst such as sulfuric acid, hydrochloric acid and any one of or a combination of the acid illustrated below in Table I,

TABLE I

Catalysts for Esterification (1) Hydrochloric acid or hydrobromic acid
(2) Sulfuric acid
(3) $C_{1-3}$ alkanoic acid e.g. acetic acid
(4) Phosphoric acid
(5) Trifluoroacetic acid or anhydride
(6) Trichloroacetic acid
(7) p-Toluenesulfonic acid or other arylsulfonic acids
(8) Acidic ion-exchange resins with calcium sulfate
(9) Polymer-protected aluminum chloride, e.g., a complex between anhydrous aluminum chloride and polystyrene-divinyl benzene copolymer diphenylphosphitepyridine
(10) A Lewis acid such as boron trifluoride
(11) Aromatic sulfonylchloride-pyridine, e.g., p-toluenesulfonylchloride
(12) triphenylphosphine ditriflate
(13) dicyclohexylcarbodiimide (DCCD)
(14) $\beta$-trichloromethyl-$\beta$-pro-piolactone
(15) N,N'-carbonyldimidazole
(16) triphenylphosphinediethylazodicarbonylate
(17) 6-chlorobenzensulfonyloxybenzotriazole
(18) 1-methyl-2-halopyridinium iodide-tertiary amine (e.g., triethylamine). at from about 0° to about 150° C. with or without refluxing until the esterification is substantially complete. Optionally, a solvent may be used to facilitate the reaction. The common solvents used are benzene, toluene, xylene, sulfolane-xylene, diethylether, tetrahydrofuran, 1,2-dimethoxyethane, dioxane and the like;

(2) A compound of formula (I) or (II) is converted to an acid halide such as acid chloride or bromide via treatment with a halogenating agent such as thionyl chloride, phosphorus penta- or oxychloride followed by reaction with an appropriate alcohol; and (3) Other methods such as alkylation of carboxylate salts (e.g., $K^+$, $Na^+$, $Ca^{++}$, $Ag^+$, $Cu^+$, tetralkylammonium-$R_4N^+$, and $Hg^{++}$ salts) of formula (I) or (II) with alkyl halides, for example, benzylchloride, benzyhydryl chloride; reaction with alkyl isoureas; treatment with diazomethane or diazophenylmethane ($C_6H_5CHN_2$); alcoholysis of anhydride derived from the cephalosporin acid corresponding to formula (I) or (II); transesterification with t-butyl esters or i-propenyl acetate and the like may also be used. These methods are disclosed in Saul Patai, editor, *The Chemistry of Functional Groups*, Supplement B, *The Chemistry of Acid Derivatives*, pp. 411-436, John Wiley & Sons, Chichester-New York-Brisbane-Torronto, 1979, and are incorporated herein by reference.

The starting penem carboxylic acids are either known or can be prepared from known procedures as illustrated in the following table:

TABLE II
Synthesis of Penem Carboxylic Acids

| Conversion | Reference |
|---|---|
| [structure: β-lactam with S-C(ORa)-S → penem with ORa, COOH] | GB 2,042,508A |
| [structure: β-lactam with S-C(Ra)-O → penem with Ra, COOH] | U.S. Pat. No. 4,169,833 |
| Preparation of: [structure with OH, S, M, COOH on penem] | U.S. Pat. No. 4,301,074, |
| [structure: β-lactam with S-C=CH(OCORa)(OCORa) with S=O → penem with OCORa] | G.B. 2,043,639 |
| [structure: β-lactam with OAc → penem with S, M, COOH] | G.B. 2,013,674 |
| Preparation of: [structure with RaO, S, M, COOH on penem] | M. Foglio et al., Heterocycles, 16,1919(1981) |
| Preparation of optically active penems from penicillins | I. Ernest, J. Gostali and R. B. Woodward; J. Am. Chem. Soc., 101, 6301(1979) |

C. Utility of the compounds within the scope of the invention

This invention also relates to a method of treatment for patients (or mammalian animals raised in the dairy, meat, or fur industries or as pets) suffering from inflammation or pain. More specifically, it relates to a method of treatment involving the administration of a compound of formula (I) or (II) as the active constituent.

For the treatment of inflammation and pain a compound of formula (I) or (II) may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be
(1) suspending agents such as sodium carboxymethylcellulose, methylcellulose, hydroxypropylmethylcellulose, sodium alginate, polyvinylpyrrolidone, gum tragacanth and gum acacia;
(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyetylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3)esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of (I) or (II) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order from about 1 mg to about 100 mg per kilogram of body weight per day are useful in the treatment of the above-indicated conditions (from about 50 mg to about 5 gms. per patient per day). For example, inflammation is effectively treated and antipyretic and analgesic activity manifested by the administration from about 2.5 to about 75 mg of the compound per kilogram of body weight per day (about 75 mg to about 3.75 gms per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological evidence in support of utility of the invention

This invention also relates to a method of treating inflammation in patients using a compound of Formula (I) or (II), particularly an especially preferred compound as the active constituent.

It has been found that the compounds of Formula (I) or (II) have anti-inflammatory/antidegeneration activity as shown below in Tables III and IV by the effective inhibition of the proteolytic function of human granulocyte elastase.

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors ($\beta$-lactam derivatives) to be tested dissolved in DMSO just before use.

Assay Procedure

To 1.0 ml of 0.2 mM Boc-AAPAN in a cuvette, 0.01–0.1 ml of DMSO with or without inhibitor was added. After mixing, a measurement was taken at 410 m$\mu$ to detect any spontaneous hydrolysis due to presence of test compound. 0.05 Milliliters of PMN extract was then added and the $\Delta$OD/min at 410 m$\mu$ was measured and recorded. Beckman model 35 spectrophotometer was used.

Results

TABLE III

| $R_1$ | n | M | B | $IC_{50}$ ($\mu$g/ml) |
|---|---|---|---|---|
| H | 0 | $CH_3$ | $OCH_2C_6H_5$ | 4 |
| H | 1 | $CH_3$ | $OCH_2C_6H_5$ | 15 |
| $(CH_3)_2CH-$ | 0 | $CH_2C_6H_5$ | $OCH_2C_6H_5$ | 0.6 |
| $(CH_3)_2CH-$ | 0 | $C_6H_5$ | $OCH_2C_6H_5$ | 1.0 |
| $CH_3O-$ | 0 | $CH_2OCOCH_3$ | $OCH_2C_6H_5$ | 4.0 |
| $CH_3CH(OH)-$ | 0 | $SC_2H_5$ | $OCH_2(p-NO_2-C_6H_5)$ | 2.0 |
| $CH_3CH(OCOOCH_2C_6H_5)-$ | 0 | $SC_2H_5$ | $OCH_2(p-NO_2-C_6H_5)$ | 0.2 |
| $(CH_3)_2CH-$ | 0 | $SC_2H_5$ | $OCH_2C_6H_5$ | 3.0 |
| $(CH_3)_2CH-$ | 0 | $CH_2-S-$ (methyltetrazole) | $OCH_2C_6H_5$ | 0.7 |
| H | 0 | $OC_2H_5$ | $OCH_2C_6H_5$ | 2.0 |
| $C_2H_5$ | 0 | $C_6H_5$ | $OCH_2C_6H_5$ | 0.3 |

TABLE IV

| $B_1$ | $IC_{50}$ ($\mu$g/ml) |
|---|---|
| H (clavulanic acid) | inactive |
| $-CH_2C_6H_5$ | 3 |

PROTOCOL

Enzyme Assays for the Inhibition of Human Polymorphonuclear Leukocyte Elastase Via Hydrolysis of N-t-Boc-alanyl-alanyl-prolylalanine-p-nitroanilide Reagents:

0.05M TES (N-tris[hydroxymethyl]methyl-2-aminoethanesulfonic acid) buffer, pH 7.5.

0.2 mM N-t-Boc-alanyl-alanyl-prolyl-alanine-p-nitroanilide (Boc-AAPAN).

Results were reported as $ED_{50}$, i.e., effective dosage in micrograms per milliliter ($\mu$g/ml) for 50% inhibition of the enzyme activity 2 minutes after zero time.

Comments

The elastase activity in the crude PMN extract may vary from one preparation to another. A control of each new batch is run, and the volume added in the assay procedure is adjusted according to activity.

The following examples illustrate the invention.

EXAMPLE 1

Benzyl 2-phenylpenem-3-carboxylate

Step A: Preparation of 4-(Triphenylmethylthio)azetidin-2-one

Sodium hydride (60%) (330 mg) was washed 3 times with hexane, suspended in dimethylformamide (DMF) (10 ml) and cooled to 0° C. under nitrogen. Triphenylmethyl mercaptan (2.4 g) in DMF (5 ml) was added dropwise over 10 minutes. The mixture was stirred for another 15 minutes before 4-(acetoxy)azetidin-2-one (1.0 g) in DMF (10 ml) was added dropwise over 15 minutes. After 15 minutes at 0° C., the reaction was quenched into cold, saturated ammonium chloride solution and extracted with ether (3x). Each ether extract was washed (brine), dried (Na$_2$SO$_4$) and evaporated. The residue was purified by flash chromatography with a solvent gradient of 25 to 40% ethyl acetate/hexane to afford 4-(triphenylmethylthio)azetidin-2-one (2.5 g) as a foam.

NMR δ(CDCl$_3$): 2.80 (1H, dm, J=15 Hz), 3.24 (1H, ddd, J=15 Hz, J=5 Hz, J=1.5 Hz), 4.3–4.5 (2H, dd over am, J=5 Hz, J=2 Hz), 6.9–7.6 (15H, m).

Step B: Preparation of 4-(Triphenylmethylthio)-1-(benzyloxycarbonylhydroxymethyl)azetidin-2-one A solution of 4-(triphenylthio)azetidin-2-one (3.45 g) and benzyl glyoxylate (2.0 g) (prepared by ozonolysis of dibenzyl fumarate) in acetonitrile (30 ml) was stirred in the presence of 4 Angstrom sieves (5 g) at room temperature for 4 days. The reaction was filtered and evaporated to a yellow oil. Preparative liquid chromatography (using 40% ethyl acetate/hexane) gave 4-(triphenylmethylthio)-1-(benzyloxycarbonylhydroxymethyl)azetidin-2-one (5.0 g as two separable diastereomers.

Higher R$_f$ isomer (40% EtOAc/Hex): NMR δ(CDCl$_3$) 2.26 (2H, br. t, J=3 Hz), 3.74 (1H, br. d, J=9 Hz), 4.31 (1H, br. t, J=3 Hz), 4.96 (1H, br. d, J=9 Hz), 5.20 (2H, s), 7.0–7.6 (20H, m).

Lower R$_f$ isomer (40% EtOAc/Hex):

NMR δ(CDCl$_3$) 2.73 (2H, br. d, J=3.5 Hz), 3.70 (1H, br. d, J=7 Hz), 4.43 (1H, br. t, J=3.5 Hz), 5.17 (1H, br. d, J=7 Hz), 5.2 (2H, s), 7.0–7.5 (20H, m).

Step C: Preparation of 4-(Triphenylmethylthio)-1-(benzyloxycarbonylchloromethyl)azedtidin-2-one To a solution of 4-(triphenylmethylthio)-1-(benzyloxycarbonylhydroxymethyl)azetidin-2-one (1.0 g) and pyridine (240 μl) in tetrahydrofuran (THF) (15 ml) at 0° C. under nitrogen was added slowly thionyl chloride (180 μl). After 15 minutes the precipitate was collected by filtration and the filtrate evaporated. The residue was rapidly eluted through a short plug of silica gel using a 15 to 30% ethyl acetate/hexane solvent gradient to afford 4-(triphenylmethylthio)-1-(benzyloxycarbonylchloromethyl)azetidin-2-one (900 mg) as a 4:3 mixture of diastereomers.

NMR δ(CDCl$_3$) 2.5–2.7 (2H, d, J=4H and t, J=4.5 Hz), 4.4–4.6 (1H, m), 5.2 (2H, br. s), 5.44 and 5.67 (1H, 2s), 6.8–7.5 (20H, m).

Step D: Preparation of 4-(Triphenylmethylthio)-1[(benzyloxycarbonyl)triphenylphosphoranylidenemethyl]azetidin-2-one A solution of 4-(triphenylmethylthio)-1-(benzyloxycarbonylchloromethyl)azedtidin-2-one (850 mg), triphenylphosphine (640 mg)and 2,6-butidine (210 μl) in DMF (50 ml) was heated at 80° C. under nitrogen for 24 hours. The reaction was then cooled, diluted with ice water and extracted with ethyl acetate (2×100 ml). The ethyl acetate extracts were washed with water and brine, dried (Na$_2$SO$_4$) and evaporated. The residue was flash chromatographed with a solvent gradient of 15 to 60% ethyl acetate/hexane to afford recovered starting material (500 mg) and then 4-(triphenylmethylthio)-1-[(benzyloxycarbonyl)triphenylphosphoranylidenemethyl]azetidin-2-one (650 mg) as a white foam, R$_f$=0.20 (30% ethyl acetate/hexane).

Step E: Preparation of 4-(Phenylcarbonylthio)-1-[(benzyloxycarbonyl)triphenylphosphoranylidenemethyl]azedtidin-2-one To a solution of 4-(triphenylmethylthio)-1-[(benzyloxycarbonyl)triphenylphosphoranylidenemethyl]azetidin-2-one (200 mg) in methanol (5 ml) was added pyridine (25 μl) followed by silver nitrate (55 mg). After stirring at room temperature for 15 minutes, the precipitate was collected by filtration, washed with methanol and ether and dried in vacuo. The silver salt product (145 mg) was used directly.

The above silver salt (145 mg) was dissolved in methylene chloride (5 μl) and benzoyl chloride (41 μl) were sequentially added. After 30 min the reaction was poured into water and extracted with methylene chloride (2×). Each extract was washed with brine, dried (Na$_2$SO$_4$) and evaporated. The residue was purified by preparative TLC (1×2000 μm silica plates, 60% ethyl acetate/hexane) to afford 4-(phenylcarbonylthio)-1-[(benzyloxycarbonyl)triphenylphosphoranylidenemethyl]azetidin-2-one (90 mg), Rf=0.32 (60% ethyl acetate/hexane).

Step F: Preparation of Benzyl 2-phenylpenem-3-carboxylate

A solution of 4-(phenylcarbonylthio)-1[(benzyloxycarbonyl)triphenylphosphoranylidenemethyl]-azetidin-2-one (90 mg) in toluene (35 ml) was heated at 110°–120° C. under nitrogen for 6 hours. The toluene was evaporated in vacuo and the residue was purified by preparative TLC (2×1000 μm silica plates, 40% ethyl acetate/hexane) to give the desired benzyl 2-phenylpenem-3-carboxylate (24 mg) as a white solid.

NMR δ(CDCl$_3$) 3.48 (1H, dd, J=16 Hz, J=2 Hz), 3.80 (1H, dd, J=16 Hz, J=3.5 Hz), 5.07 (2H, s), 5.67 (1H, dd, J=3.5 Hz, J=2 Hz), 6.9–7.4 (10H, m).

EXAMPLE 2

Following the procedures described in Example 1, but starting with an appropriate 3-substituted-4-(acetoxy)azetidin-2-one as in Example 1, Step A and treating the resulting triphenylphosphoranylidenemethyl intermediate with an appropriate carbonyl or thiocarbonyl chloride as in Step E, the following benzyl penem-3-carboxylates were prepared.

| R$_1$ | R | B |
|---|---|---|
| H | CH$_3$ | CH$_2$C$_6$H$_5$ |
| H | CH$_2$C$_6$H$_5$ | CH$_2$C$_6$H$_5$ |
| C$_2$H$_5$ | C$_6$H$_5$ | CH$_2$C$_6$H$_5$ |
| i-C$_3$H$_7$ | CH$_3$ | CH$_2$C$_6$H$_5$ |
| i-C$_3$H$_7$ | CH$_2$C$_6$H$_5$ | CH$_2$C$_6$H$_5$ |
| i-C$_3$H$_7$ | C$_6$H$_5$ | CH$_2$C$_6$H$_5$ |
| i-C$_3$H$_7$ | CH$_2$S-(N-methyltetrazolyl) | CH$_2$C$_6$H$_5$ |
| i-C$_3$H$_7$ | SC$_2$H$_5$ | CH$_2$C$_6$H$_5$ |
| CH$_3$CH(OH) | SC$_2$H$_5$ | CH$_2$(p-NO$_2$C$_6$H$_4$) |

EXAMPLE 3

Benzyl 2-methylpenem-3-carboxylate-1-sulfoxide

A solution of benzyl 2-methylpenem-3-carboxylate (160 mg) in methylene chloride (10 ml) was cooled to −20? C. and m-chloroperbenzoic acid (140 mg) was added. The reaction was allowed to warm to room temperature over 2 hours and then quenched into an aqueous solution of sodium bicarbonate (5%) and sodium sulfite. The product was extracted into methylene chloride (2×) and the extracts were each washed with brine, dried (Na₂SO₄) and evaporated in vacuo. The residue was purified by preparative TLC (1×2000 μm silica plate, 60% ethyl acetate/hexane) to give benzyl 2-methylpenem-3-carboxylate-1-sulfoxide (100 mg) as a white solid.

NMR δ(CDCl₃) 2.50 (3H, s), 3.30 (1H, dd, J=5 Hz, J=16 Hz), 3.60 (1H, dd, 16 Hz, 30 Hz), 4.73 (1H, dd, 3 Hz, 5 Hz), 5.27 (2H, s), 7.3 (5H, br. s).

EXAMPLE 4 p-Nitrobenzyl 2-(ethylthio)-6-[2-(benzyloxycarbonyloxy)ethyl]penem-3-carboxylate To a solution of p-nitrobenzyl 2-(ethylthio)-6-[(2-hydroxy)ethyl]penem-3-carboxylate (20 mg) in methylene chloride (0.5 ml) at room temperature was added 4-dimethylaminopyridine (12 μl) and benzyl chloroformate (14 μl). Flash chromatography (40% ethyl acetate/hexane) of the reaction mixture without work-up gave p-nitrobenzyl 2-(ethylthio)-6-[2-(benzyloxycarbonyloxy)ethyl]penem-3-carboxylate (6 mg).

NRM δ(CDCl₃) 1.33 (3H, t, J=7 Hz), 1.50 (3H, d, J=8 Hz), 2.98 (2H, m), 3.90 (1H, m), 5.11 (2H, s), 5.3 (2H, ABq), 7.30 (5H, s), 6.78 (2H, d, J=9 Hz), 8.13 (2H, d, 9 Hz).

What is claimed is:

1. A method of treating or managing elastase-mediated diseases comprising the administration to a mammalian species in need of such treatment an effective amount of a compound of structural formula:

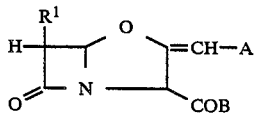

wherein
A is
 (a) hydrogen;
 (b) C₁₋₆ alkyl;
 (c) phenyl;
 (d) OR;
 (e) halo;
 (f) OCOR;
R is
 (a) hydrogen;
 (b) C₁₋₆ alkyl; or
 (c) phenyl;
R₁ is:
 (1) R'NH wherein R' is
  (a) hydrogen;
  (b) CF₃CO or CH₃OCO;
  (c) C₁₋₆ alkyl SO₂; or
  (d) C₆H₅CH₂SO₂;
 (2) hydrogen;
 (3) C₁₋₆ alkyl;
 (4) OR;
 (5) SR;
 (6) C₁₋₆ hydroxyalkyl;
 (7) C₁₋₆ alkoxycarbonyl-C₁₋₆ alkyl;
 (8) C₁₋₆ alkoxycarbonyloxy-C₁₋₆ alkyl;
 (9) benzoxycarbonyloxy-C₁₋₆ alkyl; or
 (10) phenoxycarbonyloxy-C₁₋₆ alkyl;
B is OB₁ or NHB₁ wherein B₁ is
 (1) benzyl;
 (2) phenyl;
 (3) straight or branched C₁₋₆ alkyl;
 (4) straight or branched C₂₋₈ alkenyl;
 (5) C₃₋₈ cycloalkyl;
 (6) C₁₋₆ alkanoyloxy C₋₁₋₆ alkyl;
 (7) C₁₋₆ alkanoyl C₁₋₆ alkyl;
 (8) C₁₋₆ alkoxy C₁₋₆ alkyl; or
 (9) halo=C₁₋₆ alkyl;

the above groups (1)–(9) can optionally be substituted by radicals selected from a group consisting of C₁₋₆ alkyl, hydroxy, C₁₋₆ alkoxy, halo, nitro, mercapto, amino, cyano, carboxy, sulfoamino, carbamoyl, carbamoyloxy, C₁₋₆alkyl or amino sulfonyl, C₁₋₆ alkylamino, sulfamoyl, azido, carboxamido or N-C₁₋₆ alkylcarboxamido.

2. The method of claim 1 wherein:
A is
 (a) OR; or
 (b) C₁₋₆ alkyl;
R is:
 (1) C₁₋₆ alkyl;
 (2) —CH₂—C₆H₅; or
 (3) phenyl;
R₁ is:
 (1) C₁₋₃ alkyl;
 (2) OR;
 (3) hydrogen;
 (4) benzoxycarbonyloxy-C₁₋₃ alkyl;
 (5) C₁₋₆ alkoxycarbonyloxy-C₁₋₃ alkyl; or
 (6) hydroxy-C₁₋₆ alkyl;
B is OB₁ wherein B₁ is:
 (1) benzyl;
 (2) ethyl;
 (3) t-bytyl;
 (4) —CH₂CH₂CH=CH₂;
 (5) —CH₂CHCH₂COOt—Bu;
 (6) alkanoyloxymethyl; or
 (7) alkanoylmethyl.

3. The method of claim 1 which uses

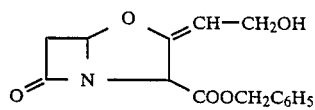

* * * * *